US012043866B2

(12) United States Patent
Judice

(10) Patent No.: US 12,043,866 B2
(45) Date of Patent: Jul. 23, 2024

(54) COMPOSITIONS AND METHODS FOR QUANTIFYING A NUCLEIC ACID SEQUENCE IN A SAMPLE

(75) Inventor: Stephen A. Judice, Portland, ME (US)

(73) Assignee: Envirologix Inc., Portland, ME (US)

( * ) Notice: Subject to any disclaimer, the term of this patent is extended or adjusted under 35 U.S.C. 154(b) by 935 days.

(21) Appl. No.: 13/816,709

(22) PCT Filed: Aug. 9, 2011

(86) PCT No.: PCT/US2011/047049
§ 371 (c)(1),
(2), (4) Date: May 28, 2013

(87) PCT Pub. No.: WO2012/021493
PCT Pub. Date: Feb. 16, 2012

(65) Prior Publication Data
US 2013/0280706 A1    Oct. 24, 2013

Related U.S. Application Data

(60) Provisional application No. 61/373,695, filed on Aug. 13, 2010.

(51) Int. Cl.
*C12Q 1/6851* (2018.01)

(52) U.S. Cl.
CPC ..... *C12Q 1/6851* (2013.01); *C12Q 2521/325* (2013.01)

(58) Field of Classification Search
None
See application file for complete search history.

(56) References Cited

U.S. PATENT DOCUMENTS

| | | | |
|---|---|---|---|
| 5,455,166 A | 10/1995 | Walker | |
| 5,629,179 A | 5/1997 | Mierendorf et al. | |
| 5,952,202 A * | 9/1999 | Aoyagi et al. | 435/91.2 |
| 6,063,604 A | 5/2000 | Wick et al. | |
| 6,130,038 A | 10/2000 | Becker et al. | |
| 6,355,421 B1 * | 3/2002 | Coull | C12Q 1/6818 435/6.11 |
| 6,617,137 B2 | 9/2003 | Dean et al. | |
| 6,794,142 B2 | 9/2004 | Laird et al. | |
| 6,977,148 B2 | 12/2005 | Dean et al. | |
| 7,056,671 B2 | 6/2006 | Enoki et al. | |
| 7,074,600 B2 | 7/2006 | Dean et al. | |
| 7,094,539 B2 | 8/2006 | Gu et al. | |
| 7,112,423 B2 | 9/2006 | Van Ness et al. | |
| 7,282,328 B2 | 10/2007 | Kong et al. | |
| 7,662,594 B2 | 2/2010 | Kong et al. | |
| 8,574,847 B2 * | 11/2013 | Becker | C12Q 1/6865 435/6.12 |
| 9,096,897 B2 | 8/2015 | Shaffer et al. | |
| 9,322,053 B2 | 4/2016 | Shaffer et al. | |
| 9,631,231 B2 | 4/2017 | Shaffer et al. | |
| 9,845,510 B2 | 12/2017 | Peters et al. | |
| 10,077,467 B2 | 9/2018 | Shaffer et al. | |
| 10,100,370 B2 | 10/2018 | Parker et al. | |
| 10,584,376 B2 | 3/2020 | Shaffer et al. | |
| 10,793,922 B2 | 10/2020 | Peters et al. | |
| 2003/0060431 A1 | 3/2003 | Simmonds et al. | |
| 2003/0211483 A1 | 11/2003 | Schroeder et al. | |
| 2005/0059003 A1 | 3/2005 | Enoki et al. | |
| 2006/0115838 A1 * | 6/2006 | Bazar | C12Q 1/6823 435/6.16 |
| 2006/0216796 A1 | 9/2006 | Hashiguchi et al. | |
| 2007/0054296 A1 * | 3/2007 | Piepenburg et al. | 435/6 |
| 2007/0082011 A1 | 4/2007 | Lehrer et al. | |
| 2008/0254458 A1 | 10/2008 | Chou | |
| 2008/0274458 A1 | 11/2008 | Latham et al. | |
| 2009/0017452 A1 | 1/2009 | Ratain et al. | |
| 2009/0017453 A1 | 1/2009 | Maples et al. | |
| 2009/0048439 A1 | 2/2009 | Weisburg et al. | |
| 2009/0081670 A1 | 3/2009 | Maples et al. | |
| 2009/0197254 A1 * | 8/2009 | Lee | 435/6 |
| 2010/0092957 A1 | 4/2010 | Zhao et al. | |
| 2010/0099149 A1 | 4/2010 | Birnboim et al. | |
| 2010/0255546 A1 | 10/2010 | Uematsu et al. | |
| 2011/0081685 A1 | 4/2011 | Makarov et al. | |
| 2011/0151467 A1 | 6/2011 | Usui et al. | |
| 2012/0021461 A1 | 1/2012 | Millar et al. | |
| 2013/0217071 A1 | 8/2013 | Montesclaros et al. | |
| 2013/0280706 A1 | 10/2013 | Judice | |
| 2014/0093883 A1 | 4/2014 | Maples et al. | |
| 2017/0044628 A1 | 2/2017 | Peters et al. | |
| 2017/0166960 A1 | 6/2017 | Shaffer et al. | |
| 2017/0327911 A1 | 11/2017 | Peters et al. | |

(Continued)

FOREIGN PATENT DOCUMENTS

| | | |
|---|---|---|
| CN | 1633505 A | 6/2005 |
| CN | 101952459 A | 1/2011 |

(Continued)

OTHER PUBLICATIONS

Holland (PNAS, 1991, 88:7276-7280).*
Li et al (Nucleic Acid Research, 2008, vol. 36, No. 6, e36, pp. 1-17).*
Paulasova (Annales de Genetique, 2004, 47:349-353).*
Dames (J Mol Diag, 2007, vol. 9, pp. 290-296).*
Dames et al., "Characterization of Aberrant Melting Peaks in Unlabeled Probe Assays", (2007) J. Mol Diag, 9: 290-296 (Year: 2007).*
Ahern, "Biochemical, reagent kits offer scientists good return on investment", (1995) The Scientist 9(15): 1-5 (Year: 1995).*
English translation of Japanese Office Action issued in JP 2015-505849, dated Mar. 31, 2015 (2 pages).

(Continued)

*Primary Examiner* — Narayan K Bhat

(74) *Attorney, Agent, or Firm* — Melissa Hunter-Ensor; Nicholas R. Ballor; Greenberg Traurig, LLP

(57) ABSTRACT

The present invention features compositions and methods for quantifying detection of a target oligonucleotide in a sample in real time. These methods are compatible with target oligonucleotides amplified using a NEAR reaction.

16 Claims, 8 Drawing Sheets

(56) References Cited

U.S. PATENT DOCUMENTS

| | | | |
|---|---|---|---|
| 2018/0363046 | A1 | 12/2018 | Shaffer et al. |
| 2020/0239947 | A1 | 7/2020 | Shaffer et al. |
| 2021/0025016 | A1 | 1/2021 | Peters et al. |

FOREIGN PATENT DOCUMENTS

| | | |
|---|---|---|
| EP | 1 201 768 A2 | 5/2002 |
| EP | 1201768 | 5/2002 |
| EP | 1 420 069 A1 | 5/2004 |
| EP | 2836609 A1 | 2/2015 |
| JP | 2002291490 | 10/2002 |
| JP | 2004532615 | 10/2004 |
| JP | 2008526228 | 7/2008 |
| JP | 2010505396 A | 2/2010 |
| JP | 2010533494 | 10/2010 |
| JP | 2011521624 A | 7/2011 |
| JP | 2014082936 A | 5/2014 |
| KR | 20040028991 A | 4/2004 |
| WO | 2002057479 | 7/2002 |
| WO | 2003008622 A2 | 1/2003 |
| WO | 200316569 | 2/2003 |
| WO | 2006074162 | 7/2006 |
| WO | 2008002920 A2 | 1/2008 |
| WO | 2008022920 A2 | 1/2008 |
| WO | 2008040126 A1 | 4/2008 |
| WO | 2009012246 A2 | 1/2009 |
| WO | 2009135093 | 11/2009 |
| WO | 2009135093 A2 | 11/2009 |
| WO | 2010107946 A2 | 9/2010 |
| WO | 2012021493 A2 | 2/2012 |
| WO | 2012022755 A | 2/2012 |
| WO | 2012022755 A1 | 2/2012 |
| WO | 2013040491 A2 | 3/2013 |
| WO | 2013155056 A1 | 10/2013 |
| WO | 2014004852 A2 | 1/2014 |
| WO | 2015168134 A1 | 11/2015 |
| WO | 2016064894 A2 | 4/2016 |
| WO | 2016069345 A1 | 5/2016 |
| WO | 2016122698 A1 | 8/2016 |

OTHER PUBLICATIONS

Office Action issued in Canadian Patent Application No. 2,869,971, dated Dec. 4, 2014 (6 pages).
International Search Report and Written Opinion, for corresponding PCT/US2011/047049, dated Mar. 16, 2012 (11 pages).
English Translation of Korean Office Action issued in Korean Patent Application No. 10-2014-7031343, dated Mar. 23, 2015 (2 pages).
Written Opinion of the International Search Authority issued in PCT/US2013/035750, dated Jul. 12, 2013 (15 pages).
Notomi, et al., "Loop-mediated Isothermal Amplification of DNA," Nucleic Acids Research, vol. 29, No. 12, Oxford University Press, 7 pages, (2000).
Office Action issued in New Zealand Patent Application No. 701145, dated Sep. 28, 2015 (3 pages).
Office Action issued in Canadian Patent Application No. 2,869,971, dated Jul. 15, 2015 (3 pages).
Office Action issued in Chinese patent application No. 201380029891. 7, dated Oct. 23, 2015 (9 pages).
Ito, et al. "Synthesis, thermal stability and resistance to enzymatic hydrolysis of the oligonucleotides containing 5-(N-aminohexyl)carbamoyl-2'-O-methyluridines", Nucleic Acids Research, 31(10), pp. 2514-2523, May 15, 2003.
Office action issued in corresponding Canadian application No. 2,810,856, dated Jun. 27, 2017 (5 pages).
Pascal, Craw. et al., "Isothermal nucleic acid amplification technologies for point-of-car-diagnostics: a critical review," Lab on a Chip, vol. 12, No. 14, Mar. 27, 2012, p. 2469, XP055057147.
Examination report for corresponding European Patent Application No. 13775206.9, dated Apr. 25, 2017 (5 pages).
Australian Office Action issued in Australian Application No. 2015246059, dated Nov. 21, 2016.
Canadian Office Action issued in Canadian Application No. 2,869,971, dated Oct. 28, 2016.
English Translation of Japanese Office Action for corresponding Japanese Application No. 2015-166615, dated Jun. 22, 2016.
European Search Report issued in European Patent Application No. 13775206, dated Oct. 8, 2015.
Office Action issued in corresponding New Zealand Application No. 701145, dated May 24, 2016.
English Translation of Third Office Action for corresponding Chinese Patent Application No. 201380029891.1, dated Feb. 4, 2017 (9 pages).
Armitage, B. et al., "Hairpin-Forming Peptide Nucleic Acid Oligomers", Biochemistry, 37, pp. 9417-9425, 1998, (1998)—Abstract only.
Office Action in corresponding Canadian application No. 2,810,856, dated May 23, 2018 (4 pages).
Office Action for corresponding Canadian Patent Application No. 2,810,856, dated Jul. 29, 2019 (3 pages).
Office Action issued in corresponding Brazilian Patent Application No. 112013004044-0, dated Mar. 23, 2020 (4 pages).
English explanation of Office Action issued in corresponding Brazilian Patent Application No. 112013004044-0, dated Mar. 23, 2020 (1 page).
Office Action in corresponding Brazilian Patent Application No. BR112013004044-0 (8 pages).
English explanation of the Office Action in corresponding Brazilian Patent Application No. BR112013004044-0 (7 pages).
Office Action received in corresponding Canadian Patent Application No. 2,810,856, dated Oct. 9, 2020 (3 pages).
Dirks et al., "Triggered amplification by hybridization chain reaction," Proceedings of the National Academy of Sciences of the United States of America, Oct. 26, 2004, vol. 101, No. 43, pp. 15275-15278.
Ehses et al., "Optimization and design of oligonucleotide setup for strand displacement amplification," Journal of Biochemical and Biophysical Methods, 2005, vol. 63, No. 3, pp. 170-186.
Krishnan et al., "Nucleic Acid Based Molecular Devices," Angewandte Chemie International Edition, Mar. 22, 2011, vol. 50, No. 14, pp. 3124-3156.
Notomi et al., "Loop-mediated isothermal amplification of DNA," Nucleic Acids Research, 2000, vol. 28, No. 12, e63, pp. 1-7.
Owczarzy et al., "IDT SciTools: a suite for analysis and design of nucleic acid oligomers," Nucleic Acids Research, 2008, vol. 36, Web Server Issue, pp. W163-W169.
"PCR Primer Design Guidelines," Premier Biosoft, www.premierbiosoft.com/tech_notes/PCR_Primer_Design.html.
"Primer Dimer," Wikipedia, the free encyclopedia, retrieved from the Internet Feb. 14, 2020 https://en.wikipedia.org/wiki/Primer_dimer.
Santangelo et al., "Dual FRET molecular beacons for mRNA detection in living cells," Nucleic Acids Research, 2004, vol. 32, No. 6, e57, pp. 1-9.
Stratagene Catalog, "Gene Characterization Kits," Stratagene Catalog, 1988, p. 39.
Thornton et al., "Real-time PCR (qPCR) Primer Design Using Free Online Software," Biochemistry and Molecular Biology Education, 2011, vol. 39, No. 2, pp. 145-154.
Yan et al., "Isothermal amplified detection of DNA and RNA," Molecular BioSystems, 2014, vol. 10, No. 5, pp. 970-1003.
Written Opinion dated Mar. 16, 2021 in corresponding Brazilian Patent Application No. BR122020012978-6 (8 pages).
English Translation of the Written Opinion dated Mar. 16, 2021 in corresponding Brazilian Patent Application No. BR122020012978-6 (7 pages).
IDT, "The Polymerase Chain Reaction," Integrated DNA Technologies, 2011, pp. 1-21.
Mann et al., "A thermodynamic approach to PCR primer design," Nucleic Acids Research, 2009, vol. 37, No. 13, e95, pp. 1-9.
Markham et al., "UNAFold: Software for Nucleic Acid Folding and Hybridization," Bioinformatics, vol. II: Structure, Function and Applications, Sep. 2, 2008, vol. 453, pp. 1-33.
Prediger, Ellen, "Designing PCR Primers and Probes," Decoded, Oct. 2013, vol. 3, No. 4, pp. 2-3.

(56) References Cited

OTHER PUBLICATIONS

Santalucia, Jr et al.,"The Thermodynamics of DNA Structural Motifs," Annual Review of Biophysics and Biomolecular Structure, Jun. 9, 2004, vol. 33, pp. 415-440.
Stofer et al., "Free Energy Calculations of Watson-Crick Base Pairing in Aqueous Solution," Journal of the American Chemical Society, 1999, vol. 121, No. 41, pp. 9503-9508.
Tyagi et al., "Molecular Beacons: Probes that Fluoresce upon Hybridization," Nature Biotechnology, Mar. 1996, vol. 14, pp. 303-308.
Untergasser et al., "Primer3—new capabilities and interfaces," Nucleic Acids Research, 2012, vol. 40, No. 15, e115, pp. 1-12.
Brazilian Office Action dated Jul. 30, 2021 in corresponding Brazilian Patent Application No. BR122020012978-6 (8 pages).
English translation of the Brazilian Office Action dated Jul. 30, 2021 in corresponding Brazilian Patent Application No. BR122020012978-6 (7 pages).
Written Opinion dated Dec. 20, 2021 in corresponding Brazilian Patent Application No. BR122020012978-6 (7 pages).
English translation of the Written Opinion dated Dec. 20, 2021 in corresponding Brazilian Patent Application No. BR122020012978-6 (6 pages).

\* cited by examiner

COMPOSITIONS AND METHODS FOR QUANTIFYING A NUCLEIC ACID SEQUENCE IN A SAMPLE

CROSS-REFERENCE TO RELATED APPLICATION

This application is the U.S. national phase application, pursuant to 35 U.S.C. § 371, of PCT International Application Ser. No. PCT/US2011/047049, filed Aug. 9, 2011, designating the United States and published as publication WO 2012/021493 A2 on Feb. 16, 2012, which claims the benefit of and priority to the following U.S. Provisional Application No. 61/373,695, filed Aug. 13, 2010, the entire contents of each of which are incorporated herein by reference.

BACKGROUND OF THE INVENTION

The polymerase chain reaction (PCR) is a technique used to amplify DNA. Typically, PCR involves thermal cycling, which consists of cycles of repeated heating and cooling of the reaction for DNA melting and enzymatic replication of the DNA using DNA polymerase, which extends from primers that bind to complementary sequences on the DNA target. Real-Time quantitative PCR (qPCR) is a techniques that is commonly used to quantify the number of copies of a given nucleic acid sequence in a biological sample. Currently, qPCR utilizes the detection of reaction products in real-time throughout the reaction and compares the amplification profile to the amplification of controls which contain a known quantity of nucleic acids at the beginning of each reaction (or a known relative ratio of nucleic acids to the unknown tested nucleic acid). The results of the controls are used to construct standard curves, to which a threshold line is drawn through the logarithmic portion of the standard curves. The threshold line is then used to interpolate the quantity of the unknowns based on where their amplification curve crosses the threshold line that was drawn from the standard control quantities.

NEAR amplification has similarities to PCR thermocycling. Like PCR, NEAR amplification employs oligonucleotide sequences which are complementary to a target sequences. In addition, NEAR amplification of target sequences results in a logarithmic increase in the target sequence, just as it does in standard PCR. Unlike standard PCR, the NEAR reaction progresses isothermally. In standard PCR, the temperature is increased to allow the two strands of DNA to separate. In a NEAR reaction, the target nucleic acid sequence is nicked at specific nicking sites present in a test sample. The polymerase infiltrates the nick site and begins complimentary strand synthesis of the nicked target nucleotide sequence (the added exogenous DNA) along with displacement of the existing complimentary DNA strand. The strand displacement replication process obviates the need for increased temperature. At this point, template molecules anneal to the displaced complementary sequence from the added exogenous DNA. The polymerase now extends from the 3' end of the template, creating a complementary strand to the previously displaced strand. The second template oligonucleotide then anneals to the newly synthesized complimentary strand and extends making a duplex of DNA which includes the nicking enzyme recognition sequence. This strand is then liable to be nicked with subsequent strand displacement extension by the polymerase, which leads to the production of a duplex of DNA which has nick sites on either side of the original target DNA. Once this is synthesized, the molecule can continue to be amplified exponentially through replication of the displaced strands with new template molecules. In addition, amplification also proceeds linearly from each product molecule through the repeated action of the nick translation synthesis at the template introduced nick sites.

The result is a very rapid increase in target signal amplification; much more rapid than PCR thermocycling, with amplification results in less than ten minutes. Quantification has been problematic. NEAR primers are separated by a nucleotide region which is too short to design a detection probe against. Detection methods that work for quantitative real-real time PCR are inapplicable to NEAR because detection molecules (i.e. molecular beacons) will be complementary to one of the primer/template oligonucleotides due to the short separation of the NEAR primer/template oligonucleotides. As such, the detection molecules will be amplified as efficiently as target DNA.

Currently, the NEAR reaction is used as an endpoint reaction that provides a very fast, but non-quantitative answer to the presence or absence of a target nucleotide sequence. Due to the high reaction rate, it is difficult to obtain a quantitative answer by arresting the reaction at any set time point or set of time points. It would be desirable if a quantitative result could be provided by monitoring the progress of the reaction in real-time.

SUMMARY OF THE INVENTION

As described below, the present invention features compositions and methods for detection of a target oligonucleotide in a sample in real time, allowing for the quantitation of the sample target oligonucleotide. These methods are compatible with target oligonucleotides amplified using a NEAR reaction.

In one aspect, the invention provides a non-amplifiable detectable polynucleotide probe, the probe contains at least about 10 nucleotides that are complementary to a target sequence, a detectable moiety, and a polymerase-arresting molecule. In one embodiment, the polymerase-arresting molecule prevents a polymerase from amplifying the probe under conditions that otherwise support polymerase activity or does not support polymerase extension. In another embodiment, the polymerase-arresting molecule is a polynucleotide adduct, a C-3 spacer, thymidine glycol, or a base substitution. In yet another embodiment, the polymerase-arresting molecule is a base substitution that maintains proper hybridization spacing with a complementary polynucleotide molecule. In yet another embodiment, the detectable moiety is a fluorophore. In yet another embodiment, the probe further contains a quencher molecule separated from the fluorophore by at least about 10-25 bases. In still another embodiment, the target sequence is double-stranded or single-stranded. In another embodiment, the portion of the probe complementary to the target sequence comprises one or more modified nucleotide. In another embodiment, the modified nucleotides are locked nucleic acids (LNAs), 2' Fluoro amidites, or 2'OMe RNA amidites. In another embodiment, the modified base(s) increase binding affinity to the target sequence.

In another aspect, the invention features a method of monitoring the production of a specific product of a nicking and extension amplification reaction, the method involving detecting a non-amplifiable detection probe which allows for the quantification of a specific product.

In another aspect, the invention features a method of quantitating a specific product in a nicking and extension amplification reaction, the method involving contacting a target nucleic acid molecule under substantially isothermal conditions with a polymerase, two primer/template oligonucleotides, each of which specifically binds to a complementary sequence on the target nucleotide molecule, a nicking enzyme, and the non-amplifiable detectable polynucleotide probe of the above aspect; generating amplicons contains at least a portion of the target nucleic acid molecule; and detecting a signal specific for oligonucleotide probe hybridization to the target nucleic acid molecule or amplicon thereof, where the signal indicates the quantity of the target nucleic acid molecule present in the sample or an amplicon thereof. In one embodiment, the detecting step does not detect an amplicon of a non-target molecule. In another embodiment, the method is carried out in real time. In another embodiment, the method provides a semi-quantitative and/or quantity threshold method of determining the amount of nucleic acid molecule present in a biological sample prior to amplification. In yet another embodiment, the method further involves the use of an amplification rate modifier to provide increased resolution of reaction products resulting from differing quantities of starting target material.

In another aspect, the invention provides a method for detecting a plurality of distinct reaction products produced in the course of a single reaction, the method involving contacting a target nucleic acid molecule under substantially isothermal conditions with a polymerase, two primer/template oligonucleotides, each of which specifically binds to a complementary sequence on the target nucleotide molecule, a nicking enzyme, and the non-amplifiable detectable polynucleotide probe of the above aspect; generating amplicons containing at least a portion of the target nucleic acid molecule; and detecting a signal specific for oligonucleotide probe hybridization to the target nucleic acid molecule or amplicon thereof, where the signal indicates the quantity of the target nucleic acid molecule present in the sample or an amplicon thereof.

In another aspect, the invention provides a method for quantifying a specific product of a nicking and extension amplification reaction, the method involving contacting a target nucleic acid molecule under substantially isothermal conditions with a polymerase, two primer/template oligonucleotides, each of which specifically binds to a complementary sequence on the target nucleotide molecule, a nicking enzyme, and the detectable oligonucleotide probe of the above aspect; generating specific products containing at least a portion of the target nucleic acid molecule; and detecting a signal indicative of oligonucleotide probe hybridization to the specific products, thereby quantifying the specific products. In one embodiment, step (c) is carried out in real time to determine the quantity of target present in the reaction.

In another aspect, the invention provides a method for monitoring in real time a nicking and extension amplification reaction, the method involving contacting the test sample with a polymerase, two primer/template oligonucleotides, each of which specifically binds to a complementary sequence on the target nucleotide molecule, a nicking enzyme, and the detectable oligonucleotide probe of the above aspect under substantially isothermal conditions; generating amplicons containing at least a portion of the target nucleic acid molecule; and detecting a signal in real time, thereby allowing the quantitation of the target nucleic acid molecule(s). In one embodiment, the test sample comprises a pathogen. In another embodiment, the pathogen is a virus, bacteria, yeast or fungus. In another embodiment, the test sample is a biological sample. In another embodiment, the biological sample is a biological fluid, cell, or tissue sample. In another embodiment, biological fluid is urine, semen, vaginal secretion, or stool. In another embodiment, the test sample is an environmental sample. In another embodiment, step (c) is carried out in real time.

In another aspect, the invention provides a detectable primer/template oligonucleotide containing a nucleic acid molecule having a double-stranded stem region and a single-stranded loop region, where at least a portion of the nucleic acid molecule is capable of hybridizing to a target nucleic acid molecule; a nicking site upstream of the portion capable of hybridizing to the target nucleic acid molecule; a RNA liable nick site within the 5' end of the target hybridizing region consisting of at least about 3-10 RNA bases of which some may be resistant to RNase activity, and which is only liable to RNase activity when present in a heteroduplex with a target molecule, a capping molecule at the 3' end of the nucleic acid molecule which does not allow polymerase extension; and a detectable moiety. In one embodiment, the capping molecule is a C3-spacer. In another embodiment, the oligonucleotide further contains a quencher moiety. In another embodiment, the fluorophore and the quencher are separated by at least about 10-25 bases. In another embodiment, the fluorophore and the quencher are separated by no more than about 4 bases and are located on disparate sides of the nick site. In another embodiment, the RNA nick site within the 5' end of the target hybridizing region may include 2'OMe RNA amidites or other RNase resistant moieties. In another embodiment, the complementary region comprises one or more modified bases having increased binding affinity to a complementary nucleotide.

In another aspect, the invention provides a method for monitoring in real time a target nucleic acid molecule in a NEAR reaction, which comprises contacting a target nucleic acid molecule under substantially isothermal conditions with a polymerase, two primer/template oligonucleotides, each of which specifically binds to a complementary sequence on the target nucleotide molecule, a nicking enzyme, a heteroduplex specific nicking enzyme, and a detectable oligonucleotide probe; generating amplicons containing a target sequence that binds the detectable oligonucleotide probe; and detecting a signal in real time, thereby quantitating the target nucleic acid molecule.

In another aspect, the invention provides a method for monitoring in real time a target nucleic acid molecule in a test sample, the method involving contacting a target nucleic acid molecule under substantially isothermal conditions with a polymerase, two primer/template oligonucleotides, each of which specifically binds to a complementary sequence on the target nucleotide molecule, a nicking enzyme, a repair enzyme or proof reading enzyme, and a detectable oligonucleotide probe; generating amplicons containing a target sequence that binds the detectable oligonucleotide probe; and detecting a signal in real time, thereby quantitating the target nucleic acid molecule. In one embodiment, the test sample comprises a pathogen (e.g., a virus, bacteria, yeast or fungus. In another embodiment, the test sample is a biological sample. In another embodiment, the biological sample is a biological fluid, cell, or tissue sample. In another embodiment, the biological fluid is urine, semen, vaginal secretion, or stool. In another embodiment, the test sample is an environmental sample. In another embodiment, step (c) is carried out in real time.

In another aspect, the invention provides a detectable circularizing oligonucleotide probe, where a portion of the 5' end of the oligonucleotide probe is complementary to a portion of the 5' end of the target nucleic acid molecule and comprises a fluorescent moiety; the 3' end of the oligonucleotide probe is complementary to a portion of the 3' end of the target nucleic acid molecule and comprises a quencher moiety; the complementary sequences at the 5' and 3' ends of the molecule are separated by a linker sequence; and the probe circularizes to bring its 5' and 3' ends into apposition when bound to a target nucleic acid molecule, thereby providing for emission of a detectable signal. In one embodiment, the linker sequence is of sufficient length to permit circularization.

In another aspect, the invention provides a method of detecting the presence and/or amount of a target nucleic acid molecule in a sample, the method containing contacting a target nucleic acid molecule with the detectable circularizing oligonucleotide probe of the above aspect, and detecting binding of the probe to a target nucleic acid molecule. In one embodiment, detection of fluorescent resonant energy transfer (FRET) indicates binding of the probe to a target sequence. In another embodiment, the absence of FRET indicates that a target nucleic acid molecule is not present in the sample.

In another aspect, the invention provides a kit for quantitating a target sequence in a NEAR reaction, the kit containing the detectable oligonucleotide probe of the above aspect and directions for use of the probe in methods of the invention.

In another aspect, the invention provides a kit for detecting a target sequence in a NEAR reaction, the kit containing the primer/template oligonucleotide of the above aspect, and directions for use of the primer/template oligonucleotide in methods of the invention.

In another aspect, the invention provides a kit for detecting a target sequence in a sample, the kit containing the detectable circularizing oligonucleotide probe of an above aspect, and directions for use of the probe in methods of the invention.

The invention provides compositions and methods for detecting a target nucleic acid molecule amplified using a NEAR reaction. Compositions and articles defined by the invention were isolated or otherwise manufactured in connection with the examples provided below. Other features and advantages of the invention will be apparent from the detailed description, and from the claims.

Definitions

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "non-amplifiable" is meant resistant to replication. Preferably, a polynucleotide sequence that is non-amplifiable cannot be replicated at a detectable level. In another embodiment, a polynucleotide sequence that is non-amplifiable is replicated at a significantly reduced level relative to a reference polynucleotide.

By "polymerase-arresting molecule" is meant a moiety associated with a polynucleotide template that prevents or significantly reduces the progression of a polymerase on the polynucleotide template. Preferably, the moiety is incorporated into the polynucleotide. In one preferred embodiment, the moiety prevents the polymerase from progressing on the template.

By "polymerase extension" is meant the forward progression of a polymerase that matches incoming monomers to their binding partners on a template polynucleotide.

By "nucleotide adduct" is meant a moiety that is bound covalently or otherwise fixed to a standard nucleotide base.

By "base substitution" is meant a substituent of a nucleobase polymer does not cause significant disruption of the hybridization between complementary nucleotide strands.

By "specific product" is meant a polynucleotide product resulting from the hybridization of template oligonucleotides to a complementary target sequence and subsequent polymerase mediated extension of the target sequence.

By "nicking and extension amplification reaction" is meant alternating cycles of nicking and extension leading to amplification of a polynucleotide of interest.

By "substantially isothermal condition" is meant at a single temperature or within a narrow range of temperatures that does not vary significantly. In one embodiment, a reaction carried out under substantially isothermal conditions is carried out at a temperature that varies by only about 1-5 C (e.g., varying by 1, 2, 3, 4, or 5 degrees). In another embodiment, the reaction is carried out at a single temperature within the operating parameters of the instrument utilized.

By "nicking enzyme" is meant a polypeptide capable of recognizing double stranded nucleic acid molecules and breaks the covalent bonds between adjoining nucleotides on a single strand.

By "amplicon" is meant a polynucleotide generated during the amplification of a polynucleotide of interest. In one example, an amplicon is generated during a polymerase chain reaction.

By "semi-quantitative" is meant providing an estimate of relative quantity based on an internal control.

By "quantity threshold method" is meant providing an estimate of quantity based on either exceeding or not exceeding in quantity a comparative standard.

By "amplification rate modifiers" is meant an agent capable of affecting the rate of polymerase extension.

By "monitoring a reaction" is meant detecting the progress of a reaction. In one embodiment, monitoring reaction progression involves detecting polymerase extension and/or detecting a complete NEAR reaction.

"Detect" refers to identifying the presence, absence or amount of the analyte to be detected.

By "detectable moiety" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "fragment" is meant a portion of a nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 10, 15, 20, 30, 40, 50, 60, 70, 80, 90, or 100 nucleotides.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

As used herein, "obtaining" as in "obtaining an agent" includes synthesizing, purchasing, or otherwise acquiring the agent.

By "reference" is meant a standard or control condition.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

By "subject" is meant a mammal, including, but not limited to, a human or non-human mammal, such as a bovine, equine, canine, ovine, or feline.

By "target nucleic acid molecule" is meant a polynucleotide to be analyzed. Such polynucleotide may be a sense or antisense strand of the target sequence. The term "target nucleic acid molecule" also refers to amplicons of the original target sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

In FIG. 1, the term Trev denotes reverse template/primer; Tfor denotes forward template/primer; SP denotes specific product; DP denotes detection probe; Pol denotes polymerase; NE denotes nicking enzyme.

DETAILED DESCRIPTION OF THE INVENTION

Figure 1A:
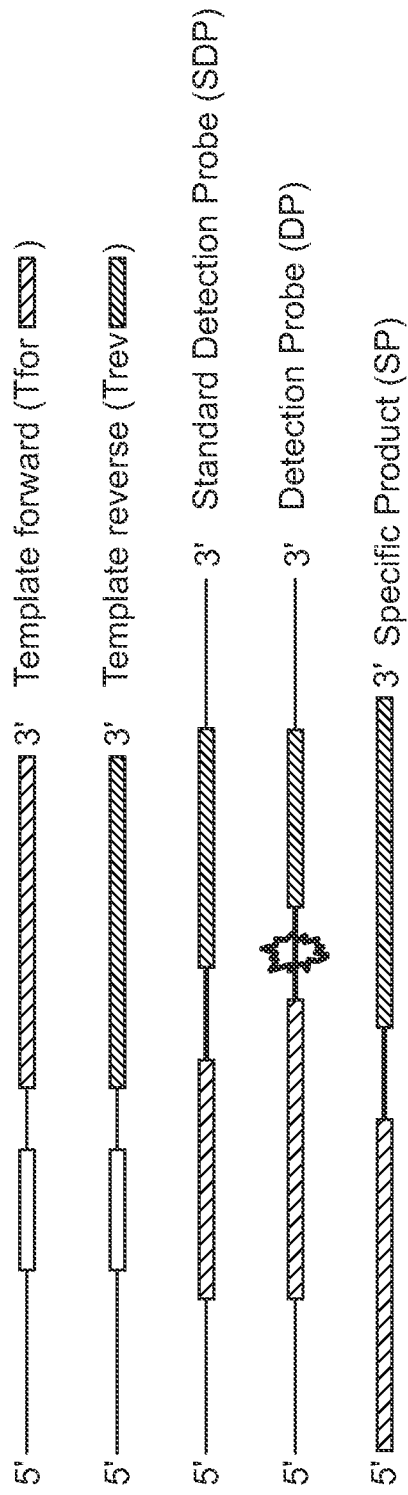
FIG. 1A is schematic diagram that illustrates template, probes, and product in the standard and Real Time NEAR Reaction. Represented in the diagram are a nicking enzyme recognition sequence, a forward template target recognition sequence, a reverse template target recognition sequence, bases in target sequence not included in templates, is the three carbon spacer (C3) in the detection probe (star burst).
Figure 1B:
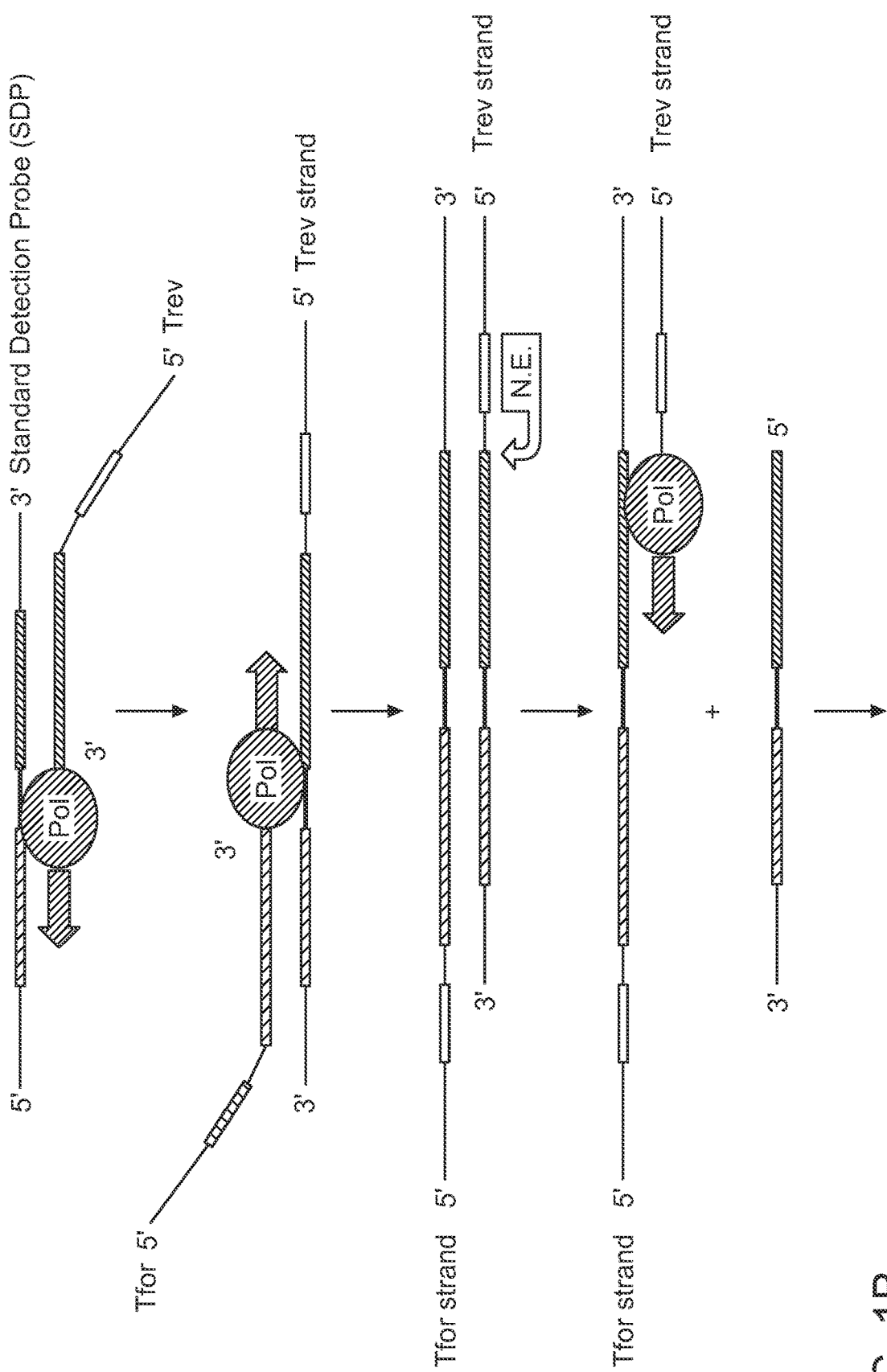
FIG. 1B is a schematic showing that a standard detection probe (SDP) can act as a target DNA if added to the NEAR reaction at the beginning of the reaction, therefore no template control (NTC) will make specific product in the presence of standard detection probe and create false positive signals. Trev binds to standard detection probe, polymerase extends, Tfor can bind to newly synthesized strand, polymerase extends, Trev binds to Tfor strand, polymerase extends, more nicking and amplification occurs. Specific produce (SP) is produced without genomic DNA being present. To make NEAR a real-time assay, the detection probe stops the polymerase from extending thereby ensuring the no template control will be negative and only the positive target reactions will continue via NEAR reaction producing specific product (SP).
Figure 1B:
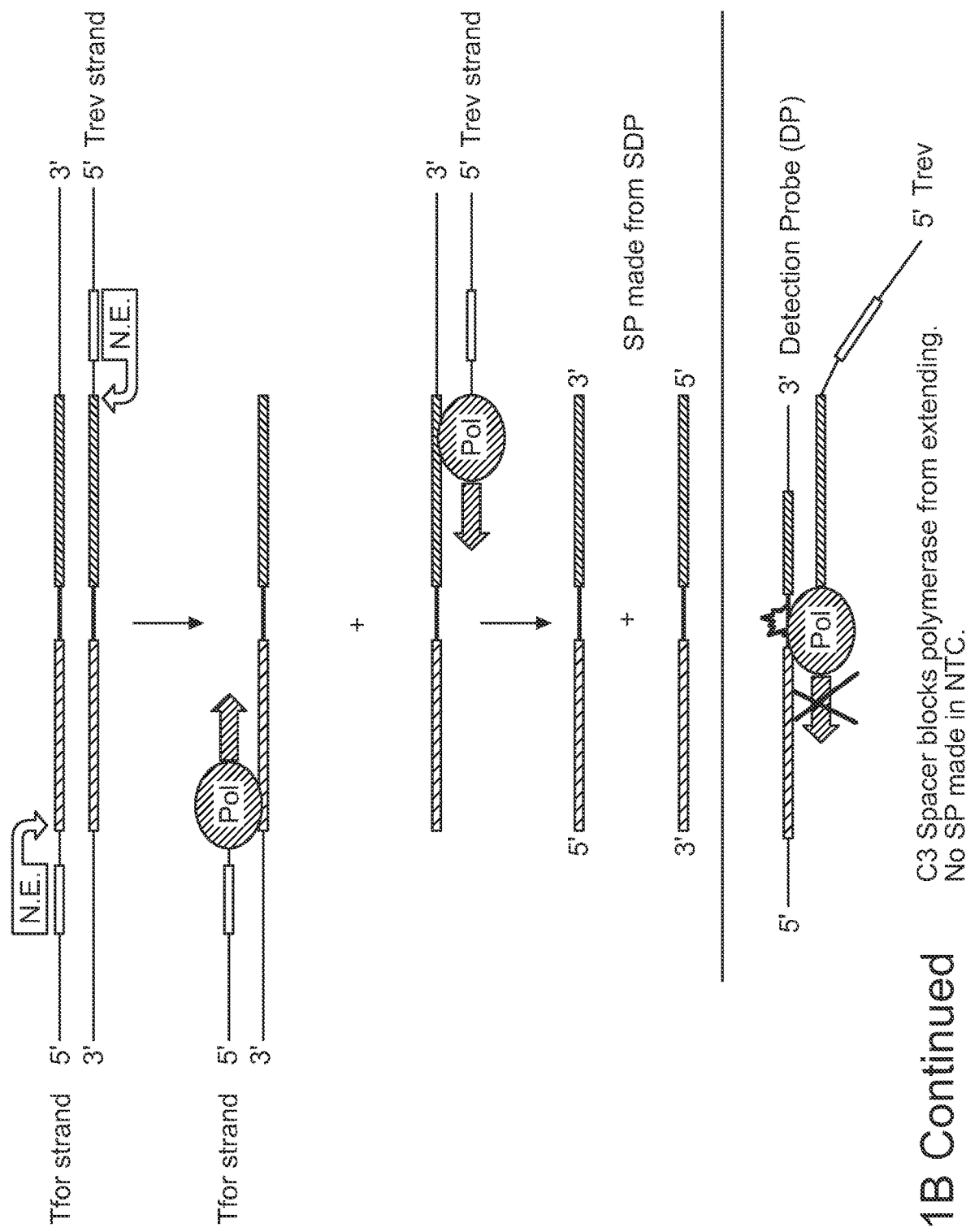

The invention features compositions and methods that are useful for quantitating a target nucleic acid molecule. In particular embodiments, the invention provides compositions and methods for quantitating a target nucleic acid molecule in a NEAR reaction (e.g., in real time).

The NEAR reaction has been used as an endpoint reaction that provides for the non-quantitative detection of target oligonucleotides. The conventional NEAR assay comprises (1) a target nucleic acid molecule; (2) two template oligonucleotide molecules (similar, but not to be confused with primer molecules of PCR) comprising some number of oligonucleotides that are complementary to the target nucleic acid molecule and a site that can be cleaved by a nicking enzyme; (3) dNTPs; (4) a strand displacing polymerase; and (5) a nicking enzyme. Current methods for quantifying the NEAR reaction, particularly in real time, are inadequate due in part to the illegitimate amplification of non-target molecules present in a sample, which can obscure detection of target amplicons in a conventional NEAR reaction. For example, there is a consistent undesirable amplification in NEAR reactions that include conventional detection probes resulting in a detectable signal in the absence of target or with signals that do not accurately reflect the amount of target nucleic acid molecule present in the reaction. Currently, the only way to overcome the amplification of detection molecule problem is to introduce a detection probe after the completion of the NEAR reaction. Although this provides for detection of an endpoint product, it fails to provide for real time monitoring of the reaction.

The present invention provides detectable oligonucleotide probes that overcome the problem of accurately quantitating a target nucleic acid molecule in a NEAR reaction. It is particularly useful for quantitating a target nucleic acid molecule in a NEAR reaction in real time. The invention is based, at least in part, on the discovery that detectable oligonucleotide probes comprising a reduction or elimination of illegitimate amplification. The detectable oligonucleotide probes of the invention are useful in NEAR reactions comprising one or more of the aforementioned NEAR components.

In one embodiment, the NEAR reaction utilizes a non-amplifiable detectable polynucleotide probe which is not aberrantly amplified in the course of a NEAR reaction. To reduce or prevent aberrant amplification or otherwise increase the accuracy of quantification, a detectable oligonucleotide probe of the invention may include one or more polymerase blocking/arresting molecules (e.g., C3-spacer, O-2-Me RNAs, thymidine glycol, AP-dC). The polymerase blocking molecules be used in conjunction with modified nucleotide base-pairing molecule(s) (e.g., locked nucleic acids (LNAs), C-5 propyne derivatives, C-5 methyl pyrimidine nucleosides, 1-[5'-O-(4,4'-Dimethoxytrityl)-D-2'-deoxyribofuranosyl]-9-(2-trifluoroacetamidoethoxy)-1,3-diaza-2-oxophenoxazine,3'-[(2-cyanoethyl)-(N,N-diisopropyl)](AP-dC), and 2,6-Diaminopurine 2'-deoxyriboside among others) that enhance binding to a target nucleotide.

Where a detectable moiety is integrated into a primer/template oligonucleotide, the polymerase arresting molecule (e.g., C3-spacer, thymidine glycol) will be synthesized on the 3' end of the primer/template oligonucleotide to prevent or reduce the formation of primer/template oligonucleotide heterodimers and homodimers, as well as aberrant extension of partial complimentary sequences in target nucleic acid sequences. the detectable primer/template oligonucleotides of the invention prevent or reduce the detection of hetero and homodimers, as well as extraneous background products that interfere with the detection of amplified target nucleic acid sequences. This will allow the detection of reaction products with simple double strand nucleic acid 'dyes' rather than fluorophore/quencher pairs in some embodiments of the invention.

Target Nucleic Acid Molecules

Methods and compositions of the invention are useful for the identification of a target nucleic acid molecule in a test sample. The target sequences is amplified from virtually any samples that comprises a target nucleic acid molecule, including but not limited to samples comprising fungi, spores, viruses, or cells (e.g., prokaryotes, eukaryotes). In specific embodiments, compositions and methods of the invention detect *Clavibacter michiganensis* subsp. *michiganensis*, *Clavibacter michiganensis* subsp. *sepedonicus*, *Pseudomonas syringae* pv Tomato, *Xanthomonas campestris* pv *Vesicatoria*, *Alternaria* spp, *Cladosporium* spp, *Fusarium oxysporum*, *Verticilium dahlia*, *Pseudomonas currugata*, *Erwina carotovora*, and *Ralstonia solanacearum*. Exemplary test samples include body fluids (e.g. blood, serum, plasma, amniotic fluid, sputum, urine, cerebrospinal fluid, lymph, tear fluid, feces, or gastric fluid), tissue extracts, culture media (e.g., a liquid in which a cell, such as a pathogen cell, has been grown), environmental samples, agricultural products or other foodstuffs, and their extracts, DNA identification tags. If desired, the sample is purified prior to inclusion in a NEAR reaction using any standard method typically used for isolating a nucleic acid molecule from a biological sample.

In one embodiment, a non-amplifiable detectable polynucleotide probe of the invention detects the presence of a pathogen in a sample. Exemplary pathogens include fungi, bacteria, viruses and yeast. Such pathogens may be detected by identifying a nucleic acid molecule encoding a pathogen protein, such as a toxin, in a test sample. Exemplary toxins include, but are not limited to aflatoxin, cholera toxin, diphtheria toxin, *Salmonella* toxin, Shiga toxin, *Clostridium botulinum* toxin, endotoxin, and mycotoxin. For environmental applications, test samples may include water, liquid extracts of air filters, soil samples, building materials (e.g., drywall, ceiling tiles, wall board, fabrics, wall paper, and floor coverings), environmental swabs, or any other sample.

Target nucleic acid molecules include double-stranded and single-stranded nucleic acid molecules (e.g., DNA, RNA, and other nucleobase polymers known in the art capable of hybridizing with a nucleic acid molecule described herein). RNA molecules suitable for detection with a detectable oligonucleotide probe or detectable primer/template oligonucleotide of the invention include, but are not limited to, double-stranded and single-stranded RNA molecules that comprise a target sequence (e.g., messenger RNA, viral RNA, ribosomal RNA, transfer RNA, microRNA and microRNA precursors, and siRNAs or other RNAs described herein or known in the art). DNA molecules suitable for detection with a detectable oligonucleotide probe or primer/template oligonucleotide of the invention include, but are not limited to, double stranded DNA (e.g., genomic DNA, plasmid DNA, mitochondrial DNA, viral DNA, and synthetic double stranded DNA). Single-stranded DNA target nucleic acid molecules include, for example, viral DNA, cDNA, and synthetic single-stranded DNA, or other types of DNA known in the art.

In general, a target sequence for detection is between 10 and 100 nucleotides in length (e.g., 10, 15, 20, 25, 30, 35, 40, 45, 50, 60, 70, 80, 90, 100 nucleotides. The GC content of the target nucleic acid molecule is selected to be less than about 45, 50, 55, or 60%. Desirably, the target sequence and nicking enzymes are selected such that the target sequence does not contain nicking sites for any nicking enzymes that will be included in the reaction mix.

Detectable Oligonucleotide Probes

The present invention provides for the quantitative detection of target nucleic acid molecules or amplicons thereof in a NEAR reaction using non-amplifiable detectable polynucleotide probes comprising at least one polymerase-arresting molecule (e.g., nucleotide modification or other moiety that renders the oligonucleotide capable of binding a target nucleic acid molecule, but incapable of supporting template extension utilizing the detectable oligonucleotide probe as a target). Without wishing to be bound by theory, the presence of one or more moieties which does not allow polymerase progression likely causes polymerase arrest in non-nucleic acid backbone additions to the oligonucleotide or through stalling of a replicative polymerase (i.e. C3-spacer, damaged DNA bases, O-2-Me bases). These constructs thus prevent or reduce illegitimate amplification of the probe during the course of a NEAR reaction. This distinguishes them from conventional detection probes, which must be added at the end of the NEAR reaction to prevent their amplification.

Conventional detection probes have proven impractical for quantitating a NEAR reaction in real time. If conventional detection probes are incorporated into the NEAR reaction, these conventional detection probes are amplified concurrently with the target. The amplification of these detection molecules masks the detection of legitimate target amplicons due to the number of starting molecules of the detection probe at the start of the reaction.

The invention provides non-amplifiable detectable polynucleotide probe that comprise least one polymerase-arresting molecule. A polymerase-arresting molecule of the invention includes, but is not limited to, a nucleotide modification or other moiety that blocks template extension by replicative DNA polymerases, thereby preventing the amplification of detection molecules; but can allow proper hybridization or nucleotide spacing to the target molecule or amplified copies of the target molecule. In one embodiment, a detectable oligonucleotide probe of the invention comprises a 3 carbon spacer (C3-spacer) that prevents or reduces the illegitimate amplification of a detection molecule.

In one embodiment, the detectable oligonucleotide probe of the invention is a hair-pin shaped oligonucleotide comprising a detectable moiety. In another embodiment, the non-amplifiable detectable polynucleotide probe is a hair-pin shaped oligonucleotide that comprises a fluorophore on one end and a quenching dye on the opposite end. The loop of the hair-pin comprises a sequence that is complementary to and capable of hybridizing with a target sequence. The stem of the hair-pin is formed by annealing of complementary arm sequences located on either side of the loop. A fluorophore and a quenching molecule are covalently linked at opposite ends of each arm. When the detectable oligonucleotide probe is in the hair pin configuration, the fluorescent and quenching molecules are proximal to one another, thereby leading to fluorescence resonance energy transfer (FRET) and quenching of the fluorescence of the fluorophore. When the detectable oligonucleotide probe encounters a target molecule, hybridization occurs; the loop structure is converted to a duplex conformation with the target molecule, causing separation of the fluorophore and quencher molecules resulting in fluorescence (Tyagi et al. Nature Biotechnology 14: March 1996, 303-308).

The detectable oligonucleotide probes are specific to the target sequence. In one embodiment, a detectable oligonucleotide probe comprises one or more modified nucleotide bases having enhanced binding affinity to a complementary nucleotide. Examples of bases include, but are not limited to locked nucleic acids (LNA), 2' Fluoro amidites, and 2'OMe RNA amidites (also functioning as a polymerase arresting molecule). Detectable oligonucleotide probes of the invention can be synthesized with different colored fluorophores and may be designed to hybridize with virtually any target sequence. In view of their remarkable specificity, a non-amplifiable detectable polynucleotide probe of the invention is used to detect a single target nucleic acid molecule in a sample, or is used in combination with detectable oligonucleotide probes each of which binds a different target nucleic acid molecule. Accordingly, the non-amplifiable detectable polynucleotide probes of the invention may be used to detect one or more target nucleic acid molecules in the same reaction, allowing these targets to be quantitated simultaneously. The present invention encompasses the use of such fluorophores in conjunction with the detectable oligonucleotide probes described herein.

Use of Non-Amplifiable Detectable Polynucleotide Probes

Non-amplifiable detectable polynucleotide probe are useful in methods for quantitating a target nucleic acid molecule in a nicking and extension amplification reaction (NEAR). The method involves contacting a target nucleic acid molecule under substantially isothermal conditions with a polymerase, two primer/template oligonucleotides, each of which specifically binds to a complementary sequence on the target nucleotide molecule, a nicking enzyme, and the detectable oligonucleotide probe in the presence of a suitable buffer and dNTPs, generating amplicons comprising at least a portion of said target nucleic acid molecule; and determining the level of target nucleic acid molecule present in the reaction by quantitating the oligonucleotide probe that hybridizes to the target nucleic acid molecule in real time during the reaction based on fluorescent intensity from the probe molecules in the reaction. Advantageously, such methods are useful for monitoring NEAR in real time.

In general, non-amplifiable detectable polynucleotide probes of the invention are included in a NEAR reaction that comprises (1) a target nucleic acid molecule; (2) two template oligonucleotide molecules comprising some number of oligonucleotides that are complementary to the target nucleic acid molecule and a site that can be cleaved by a nicking enzyme; (3) dNTPs; (4) a strand displacing polymerase; and (5) a nicking enzyme. Accordingly, the invention provides a method of using these components to quantitate a target nucleic acid molecule.

Template Design

The template oligonucleotides of the invention resemble standard NEAR template oligonucleotides, but the template oligonucleotides of the invention are designed such that the template which is complementary to a part of the detection probe is at least one base short of having its final 3' base opposite that of the polymerase blocking moiety of the detection probe.

In one working example, primer/template pairs are constructed with a stem and loop configuration. The 5' end of the primer/template oligonucleotide comprises a self-complementary region that forms at least part of the stem. The stem further encompasses at least a portion or all of the nicking enzyme recognition sequence. This nicking enzyme recognition site is linked at the 3' end to a secondary-structure-free site comprising a nicking site that is linked at the 3' end to a sequence that is complementary to a target sequence. If desired, the sequence that is complementary to the target sequence may comprise a secondary structure or may be free of secondary structure. The presence of absence or secondary structure, which may comprise a self-complementary region, will be determined to optimize the particular NEAR assay.

In one embodiment, the methods of the invention provide a NEAR reaction that comprises the standard NEAR components, but also comprises an enzyme capable of nicking a RNA nucleotide when present in a heteroduplex with a complementary DNA strand. In one example, the cleaved RNA nucleotide will be present in a string of 4-15 non-cleavable RNA nucleotides (i.e. O-2-Me-RNAs) toward the 5' end of the target complementary region of the PTO, and the 3' end of the template oligonucleotide will have a 3' terminal 'cap'. Only upon complete proper hybridization of the template oligonucleotide, with the heteroduplex cleaving molecule (i.e. RNase H) be able to cleave the RNA base, creating a 3' end for the nick translation enzyme to extend from; and allowing the NEAR reaction to progress to completion. Aberrant template binding (primer dimers, partial non-target hybridization, etc) will not lead to the RNA-DNA heteroduplex to form; and thus prevent the progression of the NEAR reaction. These templates will only be amplified after binding to a complementary nucleotide sequence through the removal of the 3' polymerase extension 'cap'. This will lead to an increased level of specificity and sensitivity of the NEAR reaction.

The template oligonucleotides of the invention are included in a NEAR reaction that comprises (1) a target nucleic acid molecule; (2) two template oligonucleotide molecules comprising some number of oligonucleotides that are complementary to the target nucleic acid molecule and a site that can be cleaved by a nicking enzyme and comprised of 4-15 RNA nucleotides, one of which is RNase liable; (3) dNTPs; (4) a strand displacing polymerase; (5) a nicking enzyme; and (6) a DNA-RNA heteroduplex RNA nicking enzyme and a 3' terminal polymerase extension cap. Accordingly, the invention provides a method of using these components to quantitate a target nucleic acid molecule.

The method involves contacting a target nucleic acid molecule under substantially isothermal conditions with a polymerase, two template oligonucleotides, each of which specifically binds to a complementary sequence on the target nucleotide molecule, a nicking enzyme, and a DNA-RNA heteroduplex nicking enzyme (e.g. RNase H) with a 3' terminal polymerase extension cap; generating a detectable amplicon that comprises at least a portion of a template oligonucleotide that binds a target sequence.

NEAR Assays

The invention provides for the detection of target nucleic acid molecules amplified in a NEAR assay. Such assays are known in the art and described herein. See, for example, US Patent Application Publication 2009/0081670, PCT Application 2009/012246, and U.S. Pat. Nos. 7,112,423 and 7,282,328, each of which is incorporated herein in its entirety. Polymerases useful in the methods described herein are capable of catalyzing the incorporation of nucleotides to extend a 3' hydroxyl terminus of an oligonucleotide (e.g., a primer/template oligonucleotide or other primer) bound to a target nucleic acid molecule. Such polymerases include those that are thermophilic and/or those capable of strand displacement. In one embodiment, a polymerase lacks or has reduced 5'-3' exonuclease activity. In other embodiments, a polymerase also has reverse transcriptase activity (e.g., Bst (large fragment), Therminator, Therminator II). Exemplary polymerases include, but are not limited to BST (large fragment), DNA polymerase I (E. coli), DNA polymerase I, Large (Klenow) fragment, Klenow fragment (3'-5' exo-), T4 DNA polymerase, T7 DNA polymerase, Deep Vent$_R$. (exo-) DNA Polymerase, Deep Vent$_R$ DNA Polymerase, DyNAzyme, High-Fidelity DNA Polymerase, Therminator, Therminator II DNA Polymerase, AmpliTherm DNA Polymerase, Taq DNA polymerase, Tth DNA polymerase, Tfl DNA polymerase, Tgo DNA polymerase, SP6 DNA polymerase, Thr DNA polymerase. The following non-limiting examples of Reverse Transcriptases (RT) can be used in the reactions of the present method to improve performance when detecting an RNA sequence: OmniScript (Qiagen), SensiScript (Qiagen), MonsterScript (Epicentre), Transcriptor (Roche), HIV RT (Ambion), SuperScript III (Invitrogen), ThermoScript (Invitrogen), Thermo-X (Invitrogen), ImProm II (Promega).

A nicking enzyme binds double-stranded DNA and cleaves one strand of a double-stranded duplex. The nicking enzyme may cleave either upstream or downstream of the binding site or nicking enzyme recognition site. In exemplary embodiments, the reaction comprises the use of a nicking enzyme that cleaves or nicks downstream of the binding site such that the product sequence does not contain the nicking site. Using an enzyme that cleaves downstream of the binding site allows the polymerase to more easily extend without having to displace the nicking enzyme. Ideally, the nicking enzyme is functional under the same reaction conditions as the polymerase. Exemplary nicking include, but are not limited to, Nt.BspQI(NEB), Nb.BbvCI (NEB), Nb.BsmI(NEB), Nb.BsrDI(NEB), Nb.BtsI(NEB), Nt.AlwI(NEB), Nt.BbvCI(NEB), Nt.BstNBI(NEB), Nt.CviPII(NEB), Nb.Bpu10I(Fermantas), and Nt.Bpu10I(Fermentas).

A NEAR reaction typically comprises nucleotides, such as, for example, dideoxyribonucleoside triphosphates (dNTPs). The reaction may also be carried out in the presence of dNTPs that comprise a detectable moiety including but not limited to a radiolabel (e.g., $^{32}P$, $^{33}P$, $^{125}I$, $^{35}S$) an enzyme (e.g., alkaline phosphatase), a fluorescent label (e.g., fluorescein isothiocyanate (FITC)), biotin, avidin, digoxigenin, antigens, haptens, or fluorochromes. The NEAR reaction further comprises certain salts and buffers that provide for the activity of the nicking enzyme and polymerase.

Advantageously, the NEAR reaction is carried out under substantially isothermal conditions where the temperature of the reaction is more or less constant during the course of the amplification reaction. Because the temperature does not need to be cycled between an upper temperature and a lower temperature, the NEAR reaction can be carried out under conditions where it would be difficult to carry out conventional PCR. Typically, the reaction is carried out at about between 35 C and 90 C (e.g., 35, 37, 42, 60, 65, 70, 75, 80, or 85 C). Advantageously, it is not essential that the temperature be maintained with a great degree of precision. Some variability in temperature is acceptable.

Melt temperature (Tm) and reaction rate modifiers may also be used to lower the melting temperature of the oligonucleotides, such as (but not limited to) ethylene glycol and glycerol. In addition, DNA polymerase reaction rate modifiers (such as dNTP and magnesium concentration) may be used to alter the reaction rate to lead to a greater quantification precision.

This invention provides methods of monitoring a NEAR reaction in real time, utilizing NEAR amplification strategy as described above and in patents US007112423B2 and US20090017452A1. In one embodiment, quantitative NEAR utilizes target nucleic acids amplification alongside a control amplification of known quantity. The amount of target nucleic acid can be calculated as an absolute quantification or a relative quantification (semi-quantitative) based on the source of the control (exogenous or endogenous control).

Quantitation of the unknown nucleotide sequence can be achieved either through comparison of logarithmic threshold amplification of the unknown to a series of known target sequences in either a separate set of reactions or in the same reaction; or as an internal endogenous or exogenous coamplification product which produces a threshold value, indicative of either a positive result (if the unknown exceeds the threshold) or negative result (if the unknown does not exceed the threshold).

Applications

The present invention provides for the real-time monitoring of the isothermic amplification NEAR reaction which can provide a quantitative measure of starting target material. Compositions and methods of the invention are useful in human diagnostics, where a rapid quantitative answer is desired. In particular embodiments, the invention provides for the use of NEAR reaction assays in human diagnostics in clinical settings. In other embodiments, the invention provides for the use of NEAR reaction assays in diagnostic field work, where access to thermocycling equipment is unavailable or would be prohibitively expensive. In still other embodiments, the invention provides for the use of NEAR reaction assays in an academic setting where rapid quantitative answers are desired.

Kits

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Currently, the NEAR reaction is used to quickly and isothermally detect the presence or absence of a target oligonucleotide in a sample. Due to technical limitations, conventional NEAR methods are unsuitable for quantifying target oligonucleotides in real time due, at least in part, to illegitimate amplification of non-target molecules in the sample, which obscures the detection and accurate quantification of target amplicons. The present invention provides compositions and methods that overcome these limitations by providing detectable oligonucleotide probes and detectable primer/templates that are not susceptible to illegitimate amplification. In one embodiment, a quantifiable NEAR assay employs a detectable oligonucleotide probe comprising one or more modifications that prevents or reduces the illegitimate amplification of non-target molecules during the NEAR reaction.

Example 1

Real Time Monitoring of a Hot Start NEAR Reaction

Reactions were carried out in a 50 µl total reaction volume that was prepared in a 50 µl/96 well format. Reactions were prepared as a two-part reaction to obtain a manual 'hot start.' If desired, an inclusive hot start may be used. The Part 1 Reaction Mix contained a final reaction concentration of 1000 nM forward template primer and 100 nM of reverse template primer, target DNA (or water and non-target DNA control); and a detection oligonucleotide at a final concentration of 200 nM. The total volume for these reactants was 5 µl. Added to the Part 1 Reaction mix was 5 µl of target containing solution per reaction. The Part 2 Reaction Mix contains the IB2 buffer (final concentration Tris HCL 50 mM; $(NH_4)_2SO_4$ 30 mM; $Na_2SO_4$ 30 mM; $MgSO_4$ 15 mM; DTT 1 mM; and Triton X-100 0.1%); dNTPs (0.3 mM final concentration); Bst Polymerase (19.2 units/reaction); and N.BstNBI nicking enzyme (15 units/reaction); diluted with water for a total volume of 40 µl. The reaction components were heated to a temperature of 56° C. for 3 minutes to preheat the reaction components. After preheating, the 40 µl Part Two Reaction Mix was added to the 10 µl Part One Reaction Mix. The reaction was allowed to continue at 56° C. for 10 minutes, followed by a 2 minute 96° C. heating step to inactivate the enzymatic activity and stop the reaction. Fluorescent intensity was measured within 20 seconds of the transfer and at 10 second intervals thereafter. Fluorescent intensity curves were analyzed via background subtracted fluorescent measurements at the collected time intervals; with graphing of data carried out with Microsoft Excel software.

Figure 2A:
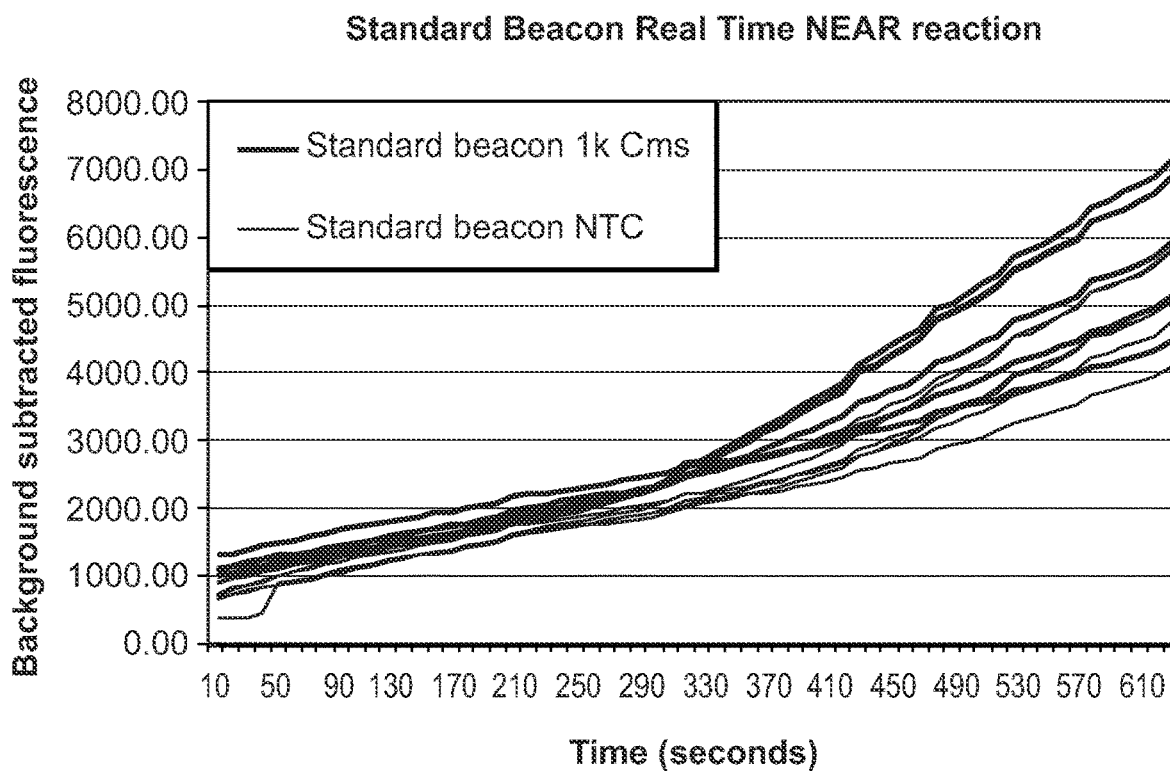
FIGS. 2A-2C are graphs showing the results of a real time reaction using a standard detection beacon (FIG. 1A) vs. a modified beacon (FIG. 1B). The modified beacon displayed a separation of target containing samples from No Target Control (NTC) samples. Melt curves of the real time reactions (FIG. 1C) containing the modified beacon with specific target; extraneous DNA with detection probe added in the reaction and post reaction, and NTC controls with detection probe added in the reaction and post reaction are shown.
Figure 2B:
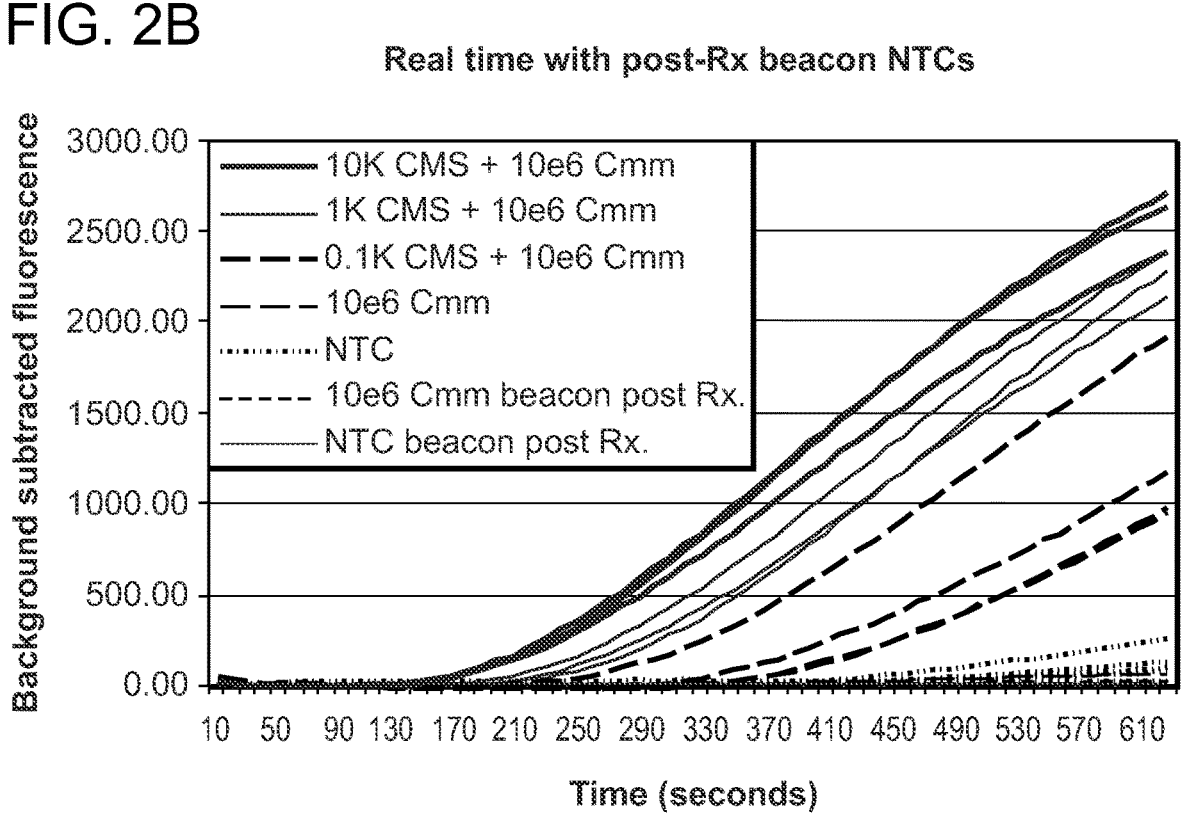
Figure 3A:
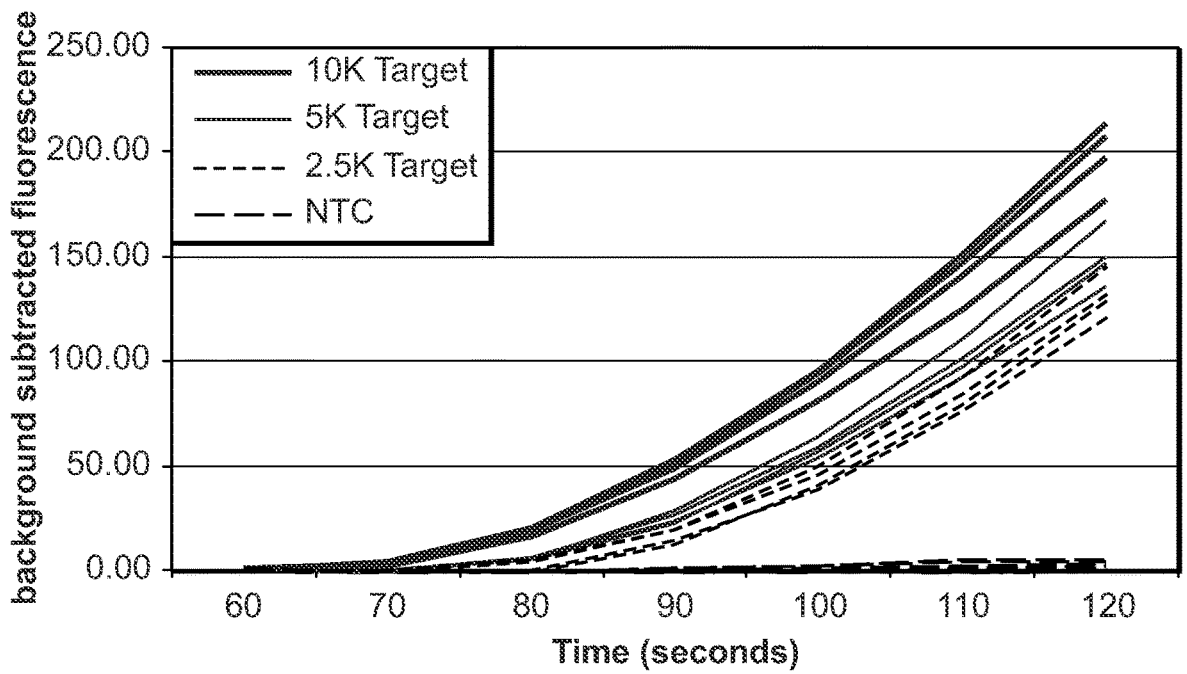
FIGS. 3A and 3B are graphs showing a real time reaction of Cms titrated in non-amplifying Cmm background DNA as 2 and 10 fold dilutions (FIGS. 2A & B respectively). Reaction was run at 56 degrees on ESE reader with 20 second read interval. Amplification of specific target (Cms) DNA provided a detectable separation from non-amplified controls within 2 minutes (FIG. 2A). Cms and Cmm denote species of bacteria *Clavibacter michiganensis* subsp. *Sepedonicus* and *Clavibacter michiganensis* subsp. *michiganensis*, respectively. The term postRX refers to post reaction.

A background subtracted graph of real time NEAR reaction shows the amplification separation of target containing samples (FIG. 2A) over NTC samples. Some lines in FIG. 2A are reactions that started with $10^4$, $10^3$, or $10^2$ copies of target genome DNA in the presence of $10^6$ copies of non-target genome DNA containing the real time detection molecule containing an internal C3-spacer as described herein above. Reactions containing this real time detection probe but no target are also shown (0 copies and $10^6$ copies of non-target genome DNA respectively) in FIG. 2A. A titration of target DNA with finer gradations ($10\times10^3$, $5\times10^3$, $2.5\times10^3$) can be found in FIG. 3B, maintaining the ability to discern between dilutions and NTC controls. Some lines in FIG. 2B represent reactions with $5\times10^3$ copies or 0 copies of target DNA, containing the standard detection probe. There was a significant separation between the 'no target control' (NTC) and the reactions containing target DNA (FIG. 2A); whereas, the standard detection probe did not present this discemable separation (FIG. 2B). This same trend was seen on a different instrument (ESE reader) which utilizes fluorescent scan frequencies every 20 seconds (FIG. 3A).

Figure 2C:
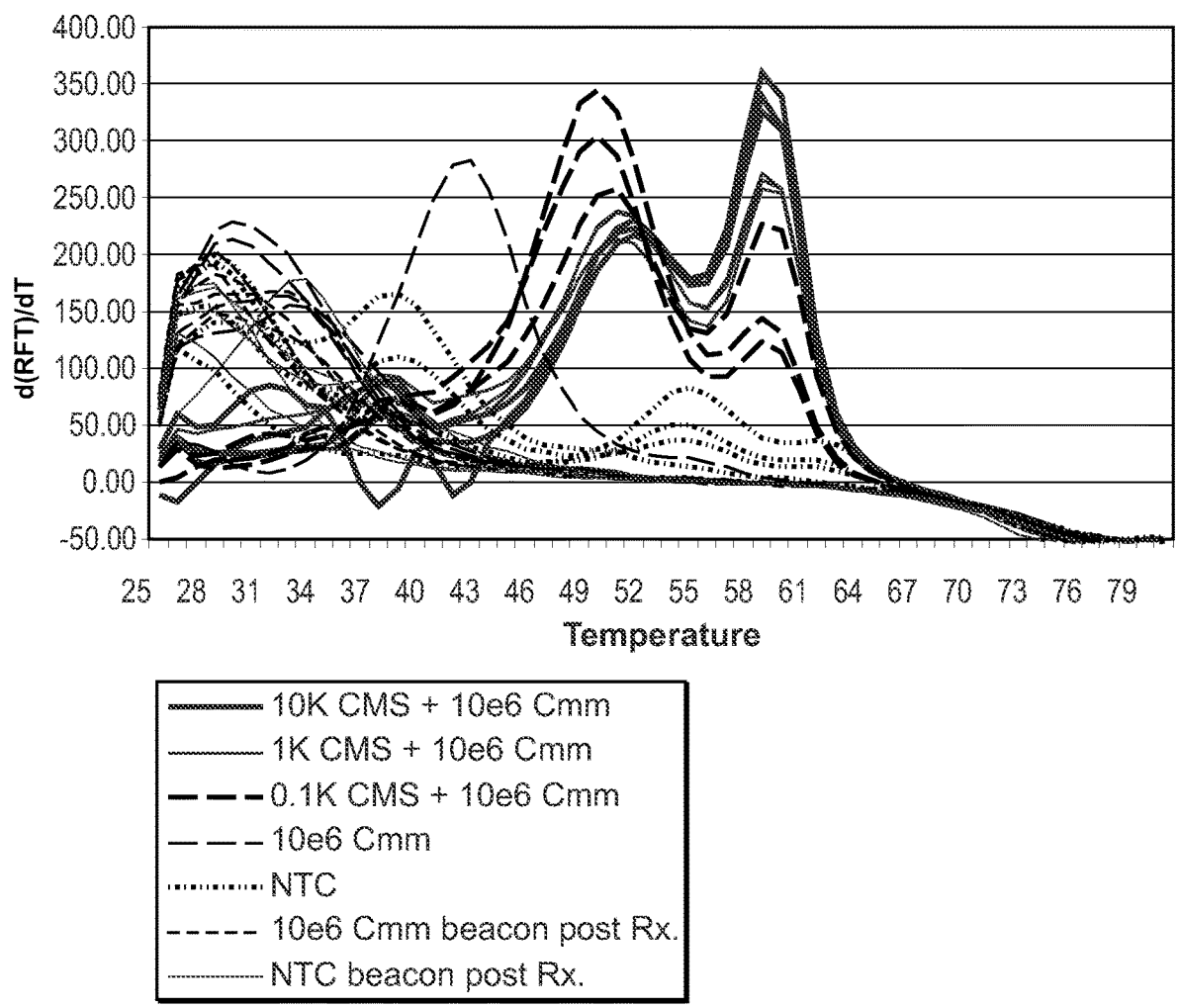
Figure 4A:
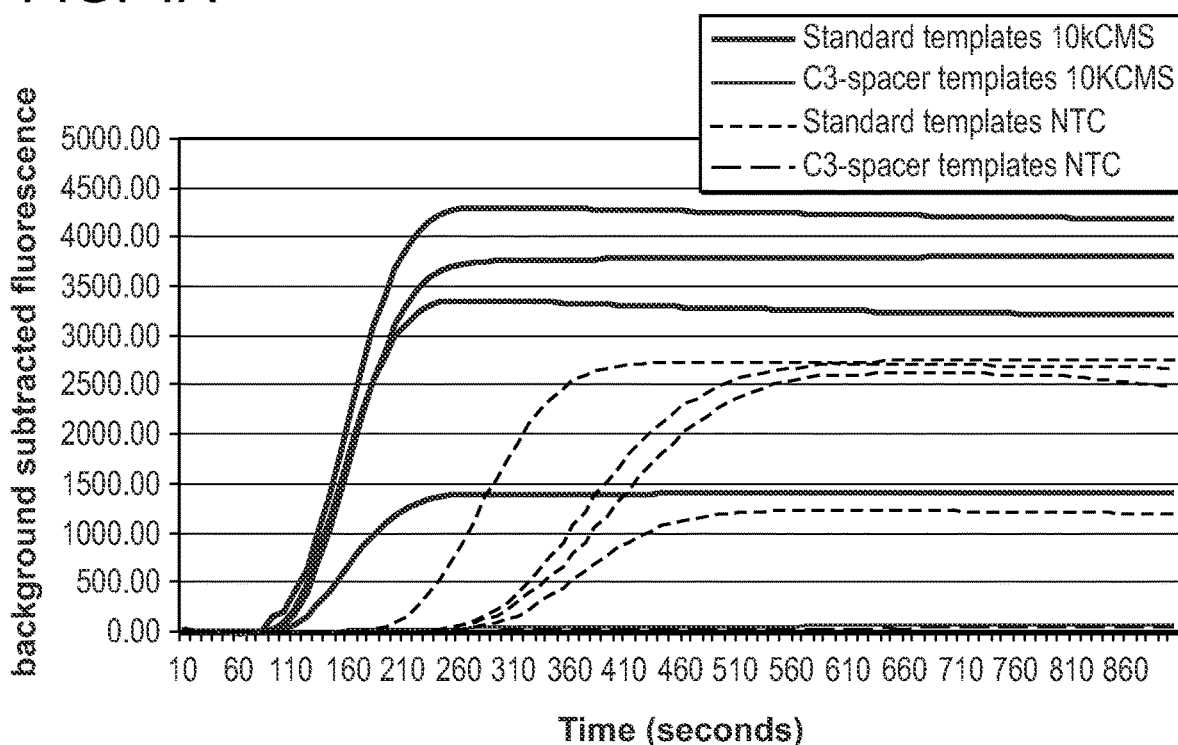
FIGS. 4A and 4B are graphs showing a real time reaction with templates containing a polymerase arresting moiety (C3-spacer), and standard templates. All reactions were run with a standard amplifiable detection molecule in the reaction. C3-spacer was located 5' to the target complementary nucleotides to prevent interference with target binding. Amplification was present in both wells with specific target and NTC of standard templates. In contrast, all wells containing polymerase arresting moiety (C-3 spacer) within the template did not support amplification.
Figure 4B:
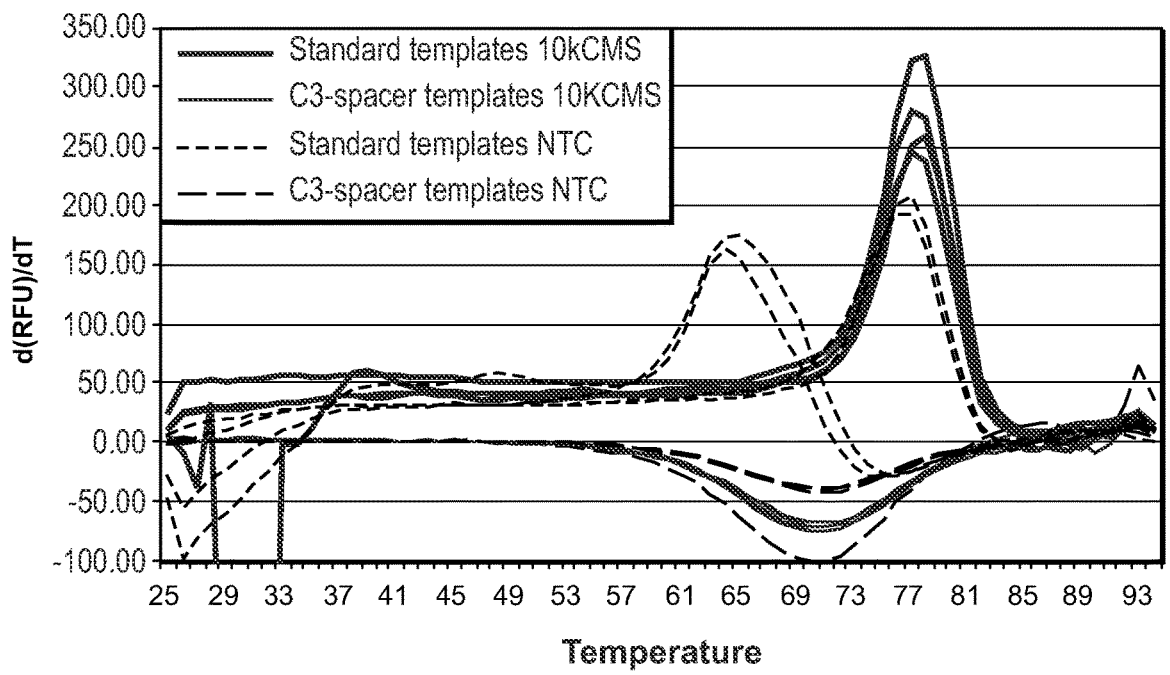

Melt curve data indicated little to no specific product production in the NTC and nontarget DNA alone containing reactions with detection probe added in the reaction as well as post-reaction (FIG. 2C). These characteristics are the hallmark of a non-amplifying probe. To further show the ability of the construct to arrest polymerase extension through the C3-spacer modification, a set of experiments was run where a C3-spacer was introduced into each template construct immediately 5' to the target complimentary region, but 3' to the nick site. This should allow the construct to bind target, but not amplify anything if the polymerase is arrested by the modification. FIGS. 4A and 4B show that there was no amplification of the templates containing the modification, whereas the normal constructs amplified the target DNA normally (as well as produce other amplification products in the NTC which bind to the detection probe in the reaction).

Example 2

Optimizing Quantification of a NEAR Assay

Figure 3B:
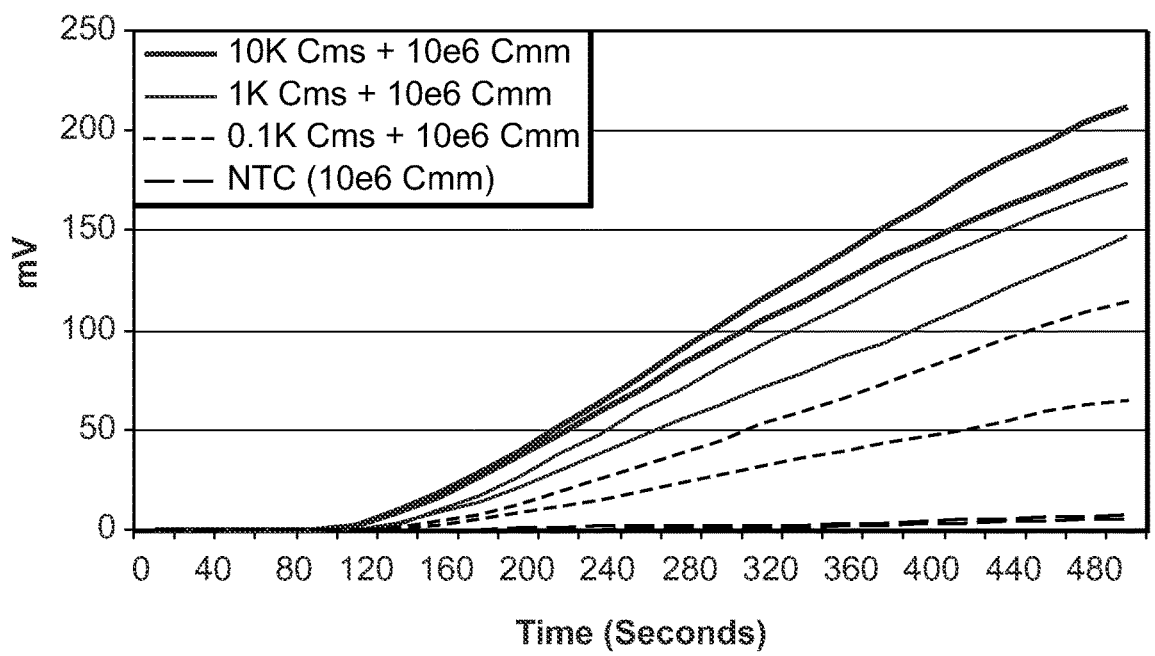

Quantitative results rely on the ability to differentiate between concentrations of substances that are being tested. FIGS. 3A and 3B display the results from target DNA titrations. These titrations were carried out by serially diluting a starting stock of purified DNA. FIG. 3 shows a clear differentiation between the concentrations of target DNA in the serially diluted samples. From these results, a standard curve can be calculated; and the amount of a target nucleic acid molecule in a sample can be determined based on the time required to amplify the target to a threshold drawn across the known DNA concentrations in the logarithmic portion of the sample amplification graph. More precise quantifications may be obtained by altering the reaction time. For example, slowing the reaction may enhance the assays ability to discriminate among target nucleic acid molecule quantities. In one embodiment, precision is increased by altering the time to logarithmic amplification. This allows improved separation of the time to cross the logarithmic threshold.

If desired, melt temperature (Tm) and reaction rate modifiers are used to lower the melting temperature of the oligonucleotides. These include, but are not limited to, ethylene glycol and glycerol. If desired, DNA polymerase reaction rate modifiers, such as dNTP and magnesium concentration, are used to alter the reaction rate and improve quantification accuracy.

Example 3

RNA Target Amplification Via Reverse Transcription (rt) NEAR in Real Time

Figures 5A, 5B:
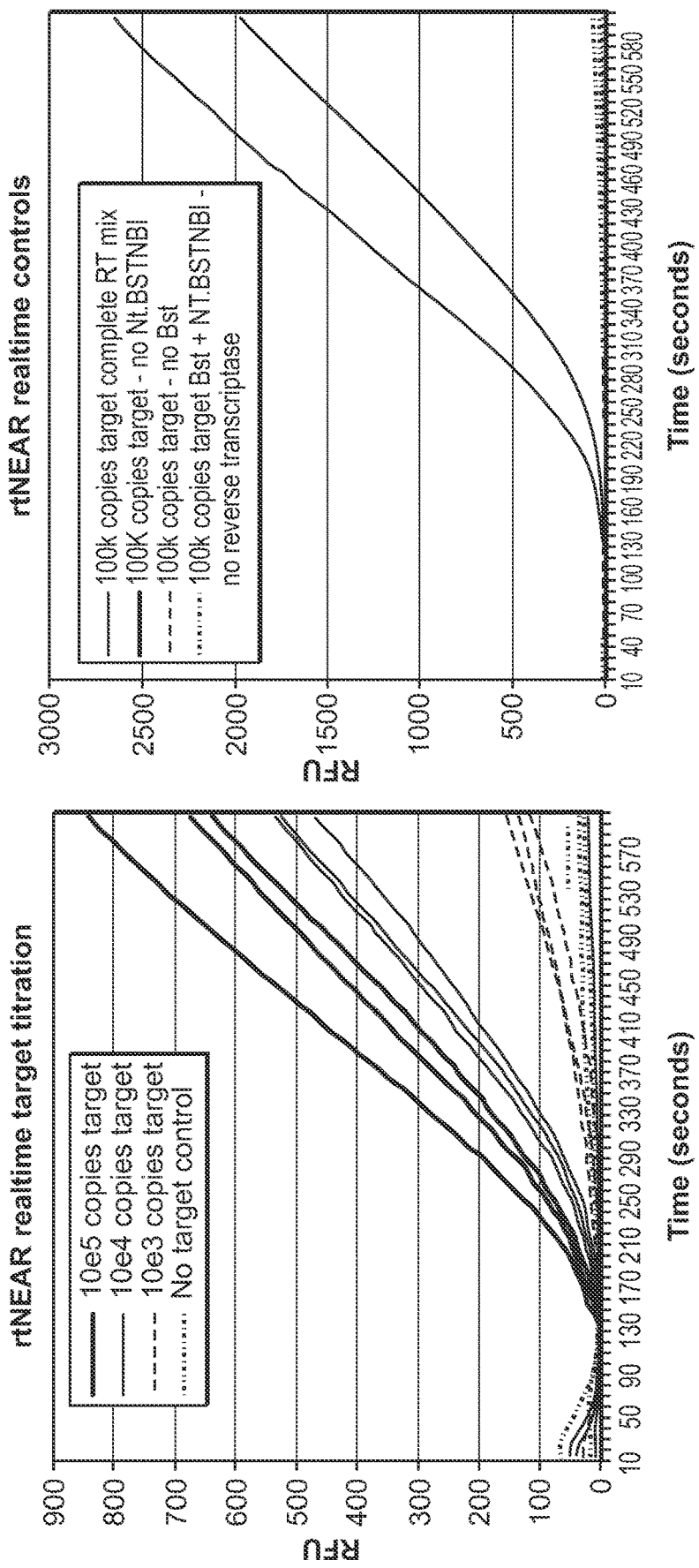
FIGS. 5A and 5B are graphs showing RNA Target Amplification via Reverse Transcription (rt) NEAR in Real Time.

FIGS. 5A and 5B are graphs showing the results of real time rt-NEAR utilizing standard templates, a RNA target, and a modified molecular beacon detection system. In addition to standard NEAR enzyme components, a reverse transcriptase was added to all reactions (FIG. 5A) to convert the RNA target into a DNA target allowing the progression of the NEAR reaction. The reactions contained 0 (No Target Control), $10^5$, $10^4$, or $10^3$ copies of a synthetic RNA oligonucleotide (FIG. 5A). Reactions lacking either NEAR enzyme components or the reverse transcriptase did not support detection of a specific product via the detection beacon (FIG. 5B) in the presence of $10^5$ copies.

Example 4

Specific Detection of a Complementary Target

The present invention further provides a detection probe that circularizes to bring its 5' and 3' ends into apposition when bound to a target nucleic acid molecule, where the 5' end is complementary to a portion of the 5' end of the target nucleic acid molecule and comprises a fluorescent moiety; the 3' end is complementary to a portion of the 3' end of the target nucleic acid molecule and comprises a quencher moiety, and the 5' and 3' ends emit a detectable signal when brought into proximity. The 5' and 3' ends are separated by a linker sequence of sufficient length to permit hybridization to the complementary sequences by the circularized detection probe. More specifically, when the oligonucleotide probe binds a complementary target sequence fluorescent resonant energy transfer (FRET) results. This configuration requires a spacer length to be equal to the length of the hybridization regions plus a minimum of 6 base pairs distance. Detection of this fluorescent resonant energy transfer identifies the presence and/or amount of a target nucleic acid molecule in a sample. Should the oligonucleotide probe bind non-specifically, FRET will not occur. This will result in the absence of FRET and/or the fluorescent emission of a different wavelength that is distinguishable from the wavelength emitted upon specific binding of a target nucleic acid molecule.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A non-amplifiable detectable polynucleotide probe, the probe comprising from 5' to 3': a fluorescent reporter, a forward template target recognition region, a polymerase-arresting molecule incorporated into the polynucleotide, a reverse template target recognition region, and a quencher molecule, wherein the fluorescent reporter and quencher molecule are separated by more than 10 bases, and wherein the polymerase-arresting molecule is selected from the group consisting of a polynucleotide adduct, 2'OMe RNA amidite, and thymidine glycol.

2. The probe of claim 1, wherein the polymerase-arresting molecule prevents interference with target binding, prevents a polymerase from amplifying the probe or does not support polymerase extension of a complementary strand.

3. The probe of claim 1, further comprising one or more modified nucleotides selected from the group consisting of locked nucleotides (LNAs), 2' Fluoro amidites, and 2'OMe RNA amidites.

4. A method of monitoring the production of a specific product of a nicking and extension amplification reaction, the method comprising detecting the non-amplifiable detection probe of claim 1.

5. A method of quantitating a specific product in a nicking and extension amplification reaction, the method comprising
   (a) contacting a target nucleic acid molecule with a polymerase, two primer/template oligonucleotides, each of which specifically binds to a complementary sequence on the target nucleic acid molecule, a nicking enzyme, and the non-amplifiable detectable polynucleotide probe of claim 1;

(b) generating amplicons comprising at least a portion of said target nucleic acid molecule; and
(c) detecting a signal specific for hybridization of the non-amplifiable detectable polynucleotide probe of claim 1 to the target nucleic acid molecule or amplicon thereof, wherein the signal indicates the quantity of the target nucleic acid molecule present in a sample or an amplicon thereof.

6. The method of claim 5, wherein the detecting step does not detect an amplicon of a non-target molecule.

7. The method of claim 5, further comprising determining the amount of at least one nucleic acid molecule present in a biological sample by a semi-quantitative and/or quantity threshold method prior to amplification.

8. The method of claim 5, further comprising using an amplification rate modifier to provide increased resolution of reaction products resulting from differing quantities of starting target material.

9. A method for detecting a plurality of distinct reaction products produced in the course of a single reaction, the method comprising:
(a) contacting a target nucleic acid molecule with a polymerase, two primer/template oligonucleotides, each of which specifically binds to a complementary sequence on the target nucleic acid molecule, a nicking enzyme, and the non-amplifiable detectable polynucleotide probe of claim 1;
(b) generating amplicons comprising at least a portion of said target nucleic acid molecule; and
(c) detecting a signal specific for hybridization of the non-amplifiable detectable polynucleotide probe of claim 1 to the target nucleic acid molecule or amplicon thereof, wherein the signal indicates the quantity of the target nucleic acid molecule present in a sample or an amplicon thereof.

10. A method for quantifying a specific product of a nicking and extension amplification reaction, the method comprising:
(a) contacting a target nucleic acid molecule with a polymerase, two primer/template oligonucleotides, each of which specifically binds to a complementary sequence on the target nucleic acid molecule, a nicking enzyme, and the detectable oligonucleotide probe of claim 1;
(b) generating specific products comprising at least a portion of said target nucleic acid molecule; and
(c) detecting a signal indicative of hybridization of the non-amplifiable detectable polynucleotide probe of claim 1 to the specific products, thereby quantifying the specific products.

11. A method for monitoring in real time a nicking and extension amplification reaction, the method comprising:
(a) contacting a test sample with a polymerase, two primer/template oligonucleotides, each of which specifically binds to a complementary sequence on a target nucleotide molecule, a nicking enzyme, and the detectable oligonucleotide probe of claim 1;
(b) generating amplicons comprising at least a portion of said target nucleic acid molecule; and
(c) detecting a signal in real time, thereby allowing the quantitation of the target nucleic acid molecule(s).

12. The method of claim 11, wherein the test sample comprises a pathogen selected from the group consisting of a virus, bacteria, yeast and a fungus.

13. A kit for quantitating a target sequence in a NEAR reaction, the kit comprising the non-amplifiable detectable polynucleotide probe of claim 1 and directions for use of the probe.

14. A method comprising using the probe of claim 1 to detect a target nucleic acid molecule in a NEAR reaction.

15. A non-amplifiable detectable polynucleotide probe, the probe comprising from 5' to 3': a fluorescent reporter, a forward template target recognition region, a polymerase-arresting molecule incorporated into the polynucleotide, a reverse template target recognition region, and a quencher molecule, wherein the fluorescent reporter and quencher molecule are separated by more than 10 bases, wherein the probe comprises one or more modified nucleotides that have enhanced binding affinity to a complementary nucleotide in a target sequence, and wherein the polymerase-arresting molecule is selected from the group consisting of a polynucleotide adduct, 2'OMe RNA amidite, and thymidine glycol.

16. A non-amplifiable detectable polynucleotide probe, the probe comprising from 5' to 3': a fluorescent reporter, a forward template target recognition region, a polymerase-arresting molecule incorporated into the polynucleotide, a reverse template target recognition region, and a quencher molecule, wherein the fluorescent reporter and quencher molecule are separated by more than 10 bases, wherein the polymerase-arresting molecule comprises a C-3 spacer, wherein the probe comprises one or more locked nucleic acids (LNAs), 2' Fluoro amidites, or 2'OMe RNA amidites, and wherein the polymerase-arresting molecule is selected from the group consisting of a polynucleotide adduct, 2'OMe RNA amidite, and thymidine glycol.

* * * * *